US012709595B2

(12) United States Patent
DiRocco et al.

(10) Patent No.: US 12,709,595 B2
(45) Date of Patent: Aug. 18, 2026

(54) SYNTHETIC PATHWAY TO BELZUTIFAN

(71) Applicant: Merck Sharp & Dohme LLC, Rahway, NJ (US)

(72) Inventors: Daniel A. DiRocco, Califon, NJ (US); Jackson Kenai Blender Cahn, Westfield, NJ (US); Wai Ling Cheung-Lee, Westfield, NJ (US); Stephanie W. Chun, Scotch Plains, NJ (US); J. Caleb Hethcox, New York, NY (US); Heather Claire Johnson, Jamaica Plain, MA (US); Jungchul Kim, Basking Ridge, NJ (US); Joshua N. Kolev, Califon, NJ (US); Birgit Kosjek, Westfield, NJ (US); Diane Le, Rahway, NJ (US); Scott D. McCann, Middlesex, NJ (US); John McIntosh, Brookline, MA (US); Jonathan P. McMullen, Scotch Plains, NJ (US); Jeffrey C. Moore, Westfield, NJ (US); William Morris, Randolph, NJ (US); Juan Esteban Velasquez Velez, Jersey City, NJ (US); Matthew S. Winston, Maplewood, NJ (US); Victoria Zhang, Bardonia, NY (US); Yong-Li Zhong, Edison, NJ (US)

(73) Assignee: Merck Sharp & Dohme LLC, Rahway, NJ (US)

(*) Notice: Subject to any disclaimer, the term of this patent is extended or adjusted under 35 U.S.C. 154(b) by 383 days.

(21) Appl. No.: 18/346,315

(22) Filed: Jul. 3, 2023

(65) Prior Publication Data

US 2024/0010613 A1 Jan. 11, 2024

Related U.S. Application Data

(60) Provisional application No. 63/359,334, filed on Jul. 8, 2022.

(51) Int. Cl.

| | |
|---|---|
| ***C07C 317/14*** | (2006.01) |
| ***C07C 315/04*** | (2006.01) |
| ***C12N 9/04*** | (2006.01) |
| ***C12P 11/00*** | (2006.01) |

(52) U.S. Cl.

CPC .......... *C07C 317/14* (2013.01); *C07C 315/04* (2013.01); *C12N 9/0006* (2013.01); *C12P 11/00* (2013.01); *C12Y 101/01* (2013.01)

(58) Field of Classification Search

CPC ... C07C 317/14; C07C 315/04; C12N 9/0006; C12P 11/00; C12Y 101/01

See application file for complete search history.

(56) References Cited

U.S. PATENT DOCUMENTS

| | | | |
|---|---|---|---|
| 9,896,418 | B2 | 2/2018 | Dixon et al. |
| 9,908,845 | B2 | 3/2018 | Dixon et al. |
| 9,969,689 | B2 | 5/2018 | Dixon et al. |
| 10,144,711 | B2 | 12/2018 | Dixon et al. |
| 10,596,366 | B2 | 3/2020 | Sama |
| 2022/0388974 | A1 | 12/2022 | Dalby et al. |

OTHER PUBLICATIONS

Kita et al. Applied and Environmental Microbiology 65.12 (1999): 5207-5211. (Year: 1999).*

Kamitori, Shigehiro, et al. "X-ray structures of NADPH-dependent carbonyl reductase from Sporobolomyces salmonicolor provide insights into stereoselective reductions of carbonyl compounds." Journal of molecular biology 352.3 (2005): 551-558. (Year: 2005).*

Zhu, Dunming, et al. "Stereoselective ketone reduction by a carbonyl reductase from Sporobolomyces salmonicolor. Substrate specificity, enantioselectivity and enzyme-substrate docking studies." Organic & Biomolecular Chemistry 4.14 (2006): 2690-2695. (Year: 2006).*

Kavanagh, K. L., et al. "Medium-and short-chain dehydrogenase/reductase gene and protein families: the SDR superfamily: functional and structural diversity within a family of metabolic and regulatory enzymes." Cellular and Molecular Life Sciences 65.24 (2008): 3895. (Year: 2008).*

Li, Hongmei, et al. "Enantioselective reduction of diaryl ketones catalyzed by a carbonyl reductase from Sporobolomyces salmonicolor and its mutant enzymes." Advanced Synthesis & Catalysis 351.4 (2009): 583-588. (Year: 2009).*

Nguyen, Phung-Hoang, et al. "Enantioselectivity and Enzyme-Substrate Docking Studies of a Ketoreductase from Sporobolomyces salmonicolor (SSCR) and *Saccharomyces cerevisiae* (YOL151w)." International Scholarly Research Notices Jan. 2014 (2014): 124289. (Year: 2014).*

Hibi, Makoto, et al. "Novel enzyme family found in filamentous fungi catalyzing trans-4-hydroxylation of L-pipecolic acid." Applied and Environmental Microbiology 82.7 (2016): 2070-2077. (Year: 2016).*

(Continued)

*Primary Examiner* — Louise W Humphrey
*Assistant Examiner* — Candice Lee Swift
(74) *Attorney, Agent, or Firm* — James T. Corcoran; Catherine D. Fitch

(57) ABSTRACT

The disclosure provides a novel process and synthetic intermediates for making belzutifan, a HIF-2α inhibitor, useful for the treatment of certain VHL-related indications and cancer.

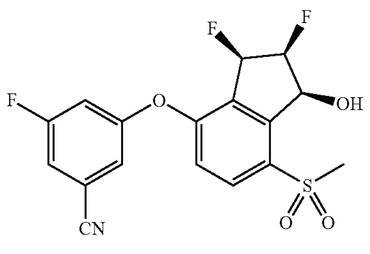

belzutifan

17 Claims, No Drawings

Specification includes a Sequence Listing.

(56) References Cited

OTHER PUBLICATIONS

Graeff, Maike, et al. "The short-chain dehydrogenase/reductase engineering database (SDRED): a classification and analysis system for a highly diverse enzyme family." Proteins: Structure, Function, and Bioinformatics 87.6 (2019): 443-451. (Year: 2019).*

NCBI; https://blast.ncbi.nlm.nih.gov/Blast.cgi; accessed Oct. 30, 2025 (Year: 2025).*

NCBI2; https://blast.ncbi.nlm.nih.gov/Blast.cgi; accessed Nov. 13, 2025 (Year: 2025).*

CD Search; https://www.ncbi.nlm.nih.gov/Structure/cdd/wrpsb.cgi; accessed Nov. 12, 2025 (Year: 2025).*

Clustal Omega; https://www.ebi.ac.uk/jdispatcher/msa/clustalo/summary?jobId=clustalo-120251112-195449-0132-8166911-p1m; accessed Nov. 12, 2025 (Year: 2025).*

PDB 1YP; https://www.rcsb.org/structure/1Y1P; accessed Nov. 17, 2025 (Year: 2005).*

PDB 1UM; https://www.rcsb.org/structure/1UJM; accessed Nov. 17, 2025 (Year: 2004).*

Wehn, Paul M. et al., Design and Activity of Specific Hypoxia-Inducible Factor-2α (HIF-2α) Inhibitors for the Treatment of Clear Cell Renal Cell Carcinoma: Discovery of Clinical Candidate (S)-3-((2,2-Difluoro-1-hydroxy-7-(methylsulfonyl)-2,3-dihydro-1H-inden-, Journal of Medicinal Chemistry, 2018, 9691-9721, 61.

Ku, Rui et al., 3-[(1S,2S,3R)-2,3-Difluoro-1-hydroxy-7-methylsulfonylindan-4-yl]oxy-5-fluorobenzonitrile (PT2977), a Hypoxia-Inducible Factor 2α (HIF-2α) Inhibitor for the Treatment of Clear Cell Renal Cell Carcinoma, Journal of Medicinal Chemistry, 2019, 6876-6893, 62.

* cited by examiner

SYNTHETIC PATHWAY TO BELZUTIFAN

CROSS-REFERENCE TO RELATED APPLICATIONS

This application is a U.S. non-provisional application which claims the benefit of U.S. Provisional Patent Application No. 63/359,334, filed Jul. 8, 2022.

REFERENCE TO SEQUENCE LISTING SUBMITTED ELECTRONICALLY

The instant application contains a Sequence Listing which has been submitted electronically in XML format and is hereby incorporated by reference in its entirety. The XML file, created on Oct. 31, 2022, is named 25555-WO-PCT_SL.XML and is 3,256 bytes in size.

FIELD OF THE INVENTION

The present disclosure relates to certain synthetic processes and intermediates which are valuable in the preparation of the therapeutic agent belzutifan.

BACKGROUND OF THE INVENTION

Intratumoral hypoxia is a driving force in cancer progression and is closely linked to poor patient prognosis and resistance to chemotherapy and radiation treatment. Hypoxia-Inducible Factors (HIF-1α and HIF-2α) are transcription factors that play central roles in the hypoxic response pathway. Under normoxic conditions, the tumor suppressor von Hippel-Lindau (VHL) protein binds to specific hydroxylated proline residues and recruits the E3 ubiquition-ligase complex that targets HIF-α proteins for proteasomal degradation. Under hypoxic conditions, HIF-α proteins accumulate and enter the nucleus to stimulate the expression of genes that regulate anaerobic metabolism, angiogenesis, cell proliferation, cell survival, extracellular matrix remodeling, pH homeostasis, amino acid and nucleotide metabolism, and genomic instability. VHL deficiency can also result in accumulated HIF expression under oxygenated conditions (pseudohypoxic conditions). Accordingly, directly targeting HIF-α proteins offers an exciting opportunity to attack tumors on multiple fronts (Keith, et al., *Nature Rev. Cancer* 12: 9-22, 2012).

Von-Hippel Lindau disease (VHL disease) is a disorder in which HIF-2α plays a significant role. VHL disease is an autosomal dominant syndrome that not only predisposes patients to kidney cancer (~70% lifetime risk), but also to hemangioblastomas, pheochromocytoma and pancreatic neuroendocrine tumors. VHL disease results in tumors with constitutively active HIF-α proteins with the majority of these dependent on HIF-2α activity (Maher, et al. *Eur. J. Hum. Genet.* 19: 617-623, 2011). HIF-2α has been linked to cancers of the retina, adrenal gland and pancreas through both VHL disease and activating mutations.

HIF-2α is also a key oncogenic driver in clear cell renal cell carcinoma (ccRCC) (Kondo, K., et al., *Cancer Cell,* 1:237-246 (2002); Maranchie, J. et al, *Cancer Cell,* 1:247-255 (2002); Kondo, K., et al., *PLoS Biol.,* 1:439-444 (2003)). In mouse ccRCC tumor models, knockdown of HIF-2α expression in pVHL (von Hippel-Lindau protein) defective cell lines blocked tumor growth comparable to reintroduction of pVHL. In addition, expression of a stabilized variant of HIF-2α was able to overcome the tumor suppressive role of pVHL.

3-[(1S,2S,3R)-2,3-Difluoro-1-hydroxy-7-methylsulfonyl-indan-4-yl]oxy-5-fluoro-benzonitrile (hereinafter, belzutifan), a novel HIF-2α inhibitor, recently received U.S. Food and Drug Administration approval for the treatment of adult patients with von Hippel-Lindau (VHL) disease who require therapy for associated renal cell carcinoma (RCC), central nervous system (CNS) hemangioblastomas, or pancreatic neuroendocrine tumors (pNET), not requiring immediate surgery.

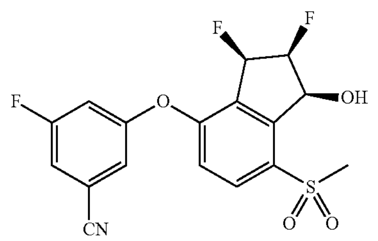

belzutifan

In a recent clinical study, 49% of patients with RCC associated with VHL disease who received belzutifan had a confirmed objective response; most patients had a reduction in renal tumor size. In addition, 30% of patients with CNS hemangioblastomas had a response after treatment with belzutifan and 91% of patients with pancreatic neuroendocrine tumors responded after treatment. Belzutifan could serve as an alternative therapy or complement surgical treatment in patients afflicted with VHL disease. Investigators hypothesize that belzutifan might delay or obviate the need for serial surgeries that can burden such patients with substantial complications. (Jonasch, E. et al., *N Engl J Med* 2021; 385:2036-2046).

In studies of belzutifan for the treatment of RCC, the agent showed excellent in vitro potency and pharmacokinetic profiles and in vivo efficacy in mouse models, and has shown encouraging outcomes in patients with advanced RCC (Xu, Rui, et al., *J. Med. Chem.* 62:6876-6893 (2019). In a recent clinical study of patients having previously treated advanced clear cell RCC, the confirmed objective response rate was 25%, and the median progression-free survival was 14.5 months. (Choueri, T. K. et al., *Nature Medicine vol.* 27, 802-805 (2021)).

Due to its therapeutic effects in treating patients suffering from VHL disease and its potential in treating patients with RCC, efficient processes for preparing large scale quantities of belzutifan to support commercial supply and continuing clinical studies are needed. U.S. Patent Application Publication No. US2022/0881407 A1 discloses methods for preparing certain substituted indanes, including belzutifan. U.S. provisional Application No. 63/191,356, filed May 21, 2021 discloses crystalline forms of certain synthetic intermediates and certain processes for isolating such forms which are advantageous for the preparation of belzutifan.

While the aforementioned publication and application describe useful and scaleable processes for preparing belzutifan, further processes for preparing the compound are valuable, particularly those that minimize the use of hazardous reagents and transition metal catalysts. The present disclosure provides such a process.

SUMMARY OF THE DISCLOSURE

The present disclosure provides a large-scale, high-yielding and convergent process for preparing belzutifan. The disclosed process minimizes use of hazardous reagents and transition metal catalysts. In addition, the disclosed process minimizes capital expenditures needed by selecting transformations for the process that can be housed or performed within conventional reactors, and does not require construction or purchase of specialized equipment.

In one aspect, the present disclosure provides a process for preparing belzutifan, comprising:

(a) contacting hydroxy indanone (5)

(5)

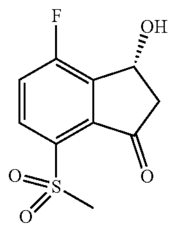

with a fluorinating agent under acidic conditions to yield fluoro hydroxyindanone (6), (6)

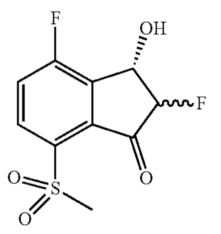

(b) contacting the fluoro hydroxyindanone (6) with a ketoreductase comprising an amino acid sequence having at least 90% sequence identify to SEQ ID NO:2 to provide fluorodiol (7), (7)

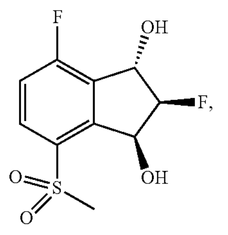

(c) isolating the fluorodiol (7), and (d) converting fluorodiol (7) to belzutifan.

In some embodiments, step (b) further comprises contacting with NADP.

In one embodiment of the process, the hydroxy indanone (5) of step (a) is prepared by contacting indanone (4)

(4)

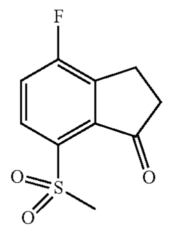

with a FoPip4H enzyme comprising an amino acid sequence having at least 90% sequence identity to SEQ ID NO:1 and a co-substrate to provide the hydroxy indanone (5).

In certain embodiments, the co-substrate is α-ketoglutarate.

In one embodiment of the process, indanone (4) is prepared by contacting bromo indanone (3)

(3)

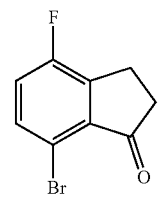

with a metabisulfite salt in the presence of a $Ni^{2+}$ catalyst and a methylating agent to provide the indanone (4).

In some embodiments, the $Ni^{2+}$ catalyst is $NiCl_2$-dppe.

In certain embodiments, the methylating agent is selected from the group consisting of trimethyl phosphate, dimethylsulfate, methyl iodide, methyl bromide, methyl chloride, dimethyl carbonate, methyl trifluoromethane sulfonate, and trimethyloxonium tetrafluoroborate.

In one embodiment of the process, the bromo indanone (3) is prepared by cyclizing phenylpropionic acid (2)

(2)

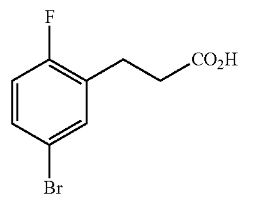

in thionyl chloride in the presence of a Lewis acid to provide indanone (3).

In one embodiment of the process, phenylpropionic acid (2) is prepared by reacting benzaldehyde (1)

(1)

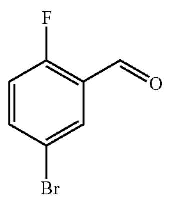

with Meldrum's acid to provide the phenylpropionic acid (1).

In one embodiment of the process, step (d) comprises: treating fluoro diol (7) with a deoxyfluorinating agent and a base to provide trifluoro indanol (8)

(8)

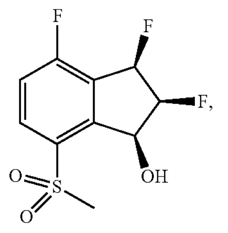

and converting trifluoro indanol (8) to belzutifan.

In one embodiment, step (d) further comprises coupling trifluoro indanol (8) with phenol (9)

(9)

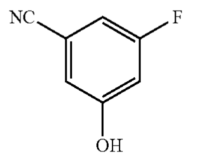

to provide belzutifan.

In specific embodiments, the coupling is conducted in an aqueous solution in the presence of a base.

In one embodiment, step (d) further comprises:

treating belzutifan with activated carbon;

recrystallizing decolorized belzutifan from a mixture of a dipolar aprotic solvent and water;

and isolating purified belzutifan.

In a second aspect, the present disclosure provides a process for preparing fluorodiol (7)

(7)

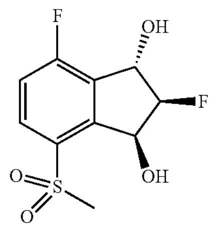

comprising:

(a) contacting hydroxy indanone (5)

(5)

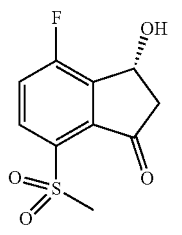

with a fluorinating agent under acidic conditions to yield fluoro hydroxyindanone (6), (6)

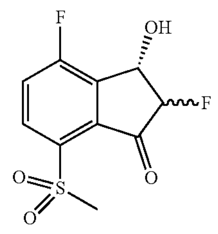

(b) contacting the fluoro hydroxyindandone (6) with a ketoreductase to provide fluorodiol (7); and (c) isolating the fluorodiol (7).

In some embodiments, step (b) further comprises contacting with NADP.

In certain embodiments, step (b) further comprises contacting with a secondary alcohol.

In specific embodiments, the ketoreductase comprises an amino acid sequence having at least a 90% sequence identity to SEQ ID NO: 2.

In a third aspect, the present disclosure provides a compound of the Formula (A)

(A)

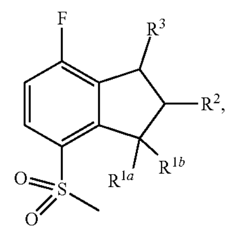

wherein:

$R^{1a}$ and $R^{1b}$ are independently H or hydroxy, or alternatively $R^{1a}$ and $R^{1b}$ together with the carbon atom to which they are attached form a carbonyl;

$R^2$ is H or fluoro;

$R^3$ is fluoro or hydroxy; and the compound is selected from the group consisting of:

(5)

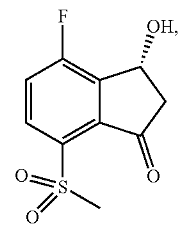

(7)

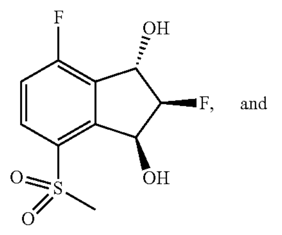

-continued (8)

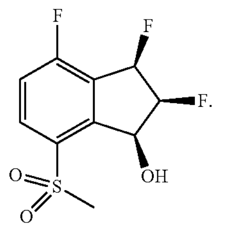

DETAILED DESCRIPTION OF THE INVENTION

Definitions

Certain technical and scientific terms are specifically defined below. Unless specifically defined elsewhere in this document, all other technical and scientific terms used herein have the meaning commonly understood by one of ordinary skill in the art to which this disclosure relates. That notwithstanding and except where stated otherwise, the following definitions apply throughout the specification and claims. Chemical names, common names, and chemical structures may be used interchangeably to describe the same structure.

As used herein, and throughout this disclosure, the following terms, unless otherwise indicated, shall be understood to have the following meanings:

The present disclosure also embraces isotopically-labelled compounds that are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine and iodine, such as $^{2}H$, $^{3}H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$, and $^{123}I$, respectively.

Certain isotopically-labelled compounds (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are particularly preferred for their ease of preparation and detectability. Isotopic substitution at a site where epimerization occurs may slow or reduce the epimerization process and thereby retain the more active or efficacious form of the compound for a longer period of time. Isotopically labeled compounds, in particular those containing isotopes with longer half-lives ($T_{1/2}>1$ day), can generally be prepared by following procedures analogous to those disclosed in the Schemes and/or in the Examples herein below, by substituting an appropriate isotopically labeled reagent for a non-isotopically labeled reagent.

Compounds herein may contain one or more stereogenic centers and can occur as racemates, racemic mixtures, single enantiomers, diastereomeric mixtures, and individual diastereomers. Additional asymmetric centers may be present depending upon the nature of the various substituents on the molecule. Each such asymmetric center will independently produce two optical isomers, and all possible optical isomers and diastereomers in mixtures and as pure or partially purified compounds are included within the disclosure. Any formulas, structures, or names of compounds described herein that do not specify a particular stereochemistry are meant to encompass any and all existing isomers as described above and mixtures thereof in any proportion. When stereochemistry is specified, the disclosure is meant to encompass that particular isomer in pure form or as part of a mixture with other isomers in any proportion.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Enantiomers can also be separated by use of chiral HPLC column.

All stereoisomers (for example, geometric isomers, optical isomers, and the like) of disclosed compounds (including those of the salts and solvates of compounds as well as the salts, solvates, and esters of prodrugs), such as those that may exist due to asymmetric carbons on various substituents, including enantiomeric forms (which may exist even in the absence of asymmetric carbons), rotameric forms, atropisomers, and diastereomeric forms, are contemplated within the scope of this disclosure. Individual stereoisomers of compounds may, for example, be substantially free of other isomers, or may be admixed, for example, as racemates or with all other, or other selected, stereoisomers. The chiral centers can have the S or R configuration as defined by the IUPAC 1974 Recommendations.

The present disclosure further includes compounds and synthetic intermediates in all their isolated forms. For example, the above-identified compounds are intended to encompass all forms of the compounds such as, any solvates, hydrates, stereoisomers, and tautomers thereof.

"Ketoreductase" and "KRED" are used interchangeably herein to refer to a polypeptide having an enzymatic capability of reducing a carbonyl group to its corresponding alcohol. More specifically, the ketoreductase polypeptides disclosed are capable of stereoselectively reducing the fluoro hydroxyindanone (6), supra to the fluorodiol (7), supra. The polypeptide typically utilizes a cofactor which is reduced nicotinamide adenine dinucleotide (NADH) or reduced nicotinamide adenine dinucleotide phosphate (NADPH). Ketoreductases as used herein include naturally occurring (wild type) ketoreductases as well as non-naturally occurring engineered polypeptides generated by human manipulation.

"Protein," "polypeptide," and "peptide" are used interchangeably herein to denote a polymer of at least two amino acids covalently linked by an amide bond, regardless of length or post-translational modification (e.g., glycosylation or phosphorylation, lipidation, myristoylation, ubiquitination, etc.). Included within this definition are D- and L-amino acids, and mixtures of D- and L-amino acids, as well as polymers comprising D- and L-amino acids, and mixtures of D- and L-amino acids. Proteins, polypeptides, and peptides may include a tag, such as a histidine tag, which should not be included when determining percentage of sequence identity.

"Amino acid" or "residue" as used in context of the polypeptides disclosed herein refers to the specific monomer at a sequence position. Amino acids are referred to herein by either their commonly known three-letter symbols or by the one-letter symbols recommended by IUPAC-IUB Biochemical Nomenclature Commission. Nucleotides, likewise, may be referred to by their commonly accepted single letter codes.

The abbreviations used for the genetically encoded amino acids are conventional and are as follows: alanine (Ala or A), arginine (Arg or R), asparagine (Asn or N), aspartate (Asp or D), cysteine (Cys or C), glutamate (Glu or E), glutamine (Gln or Q), histidine (His or H), isoleucine (Ile or I), leucine (Leu or L), lysine (Lys or K), methionine (Met or M), phenylalanine (Phe or F), proline (Pro or P), serine (Ser or S), threonine (Thr or T), tryptophan (Trp or W), tyrosine (Tyr or Y), and valine (Val or V).

"Percentage of sequence identity," "percent identity," and "percent identical" are used herein to refer to comparisons between polynucleotide sequences or polypeptide sequences, and are determined by comparing two optimally aligned sequences over a comparison window, wherein the portion of the polynucleotide or polypeptide sequence in the comparison window may comprise additions or deletions (i.e., gaps) as compared to the reference sequence for optimal alignment of the two sequences. The percentage is calculated by determining the number of positions at which either the identical nucleic acid base or amino acid residue occurs in both sequences or a nucleic acid base or amino acid residue is aligned with a gap to yield the number of matched positions, dividing the number of matched positions by the total number of positions in the window of comparison and multiplying the result by 100 to yield the percentage of sequence identity. Determination of optimal alignment and percent sequence identity is performed using the BLAST and BLAST 2.0 algorithms (see e.g., Altschul et al., 1990, J. Mol. Biol. 215: 403-410; and Altschul et al., 1977, Nucleic Acids Res. 3389-3402). Software for performing BLAST analyses is publicly available through the National Center for Biotechnology Information website.

Briefly, the BLAST analyses involve first identifying high scoring sequence pairs (HSPs) by identifying short words of length W in the query sequence, which either match or satisfy some positive-valued threshold score T when aligned with a word of the same length in a database sequence. T is referred to as, the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, M=5, N=−4, and a comparison of both strands. For amino acid sequences, the BLASTP program uses as defaults a word length (W) of 3, an expectation (E) of and the BLOSUM62 scoring matrix (see Henikoff and Henikoff, 1989, Proc. Natl. Acad. Sci. USA 89:10915).

Numerous other algorithms are available that function similarly to BLAST in providing percent identity for two sequences. Optimal alignment of sequences for comparison can be conducted, e.g., by the local homology algorithm of Smith and Waterman, 1981, Adv. Appl. Math. 2:482, by the homology alignment algorithm of Needleman and Wunsch, 1970, J. Mol. Biol. 48:443, by the search for similarity method of Pearson and Lipman, 1988, Proc. Natl. Acad. Sci. USA 85:2444, by computerized implementations of these algorithms (GAP, BESTFIT, FASTA, and TFASTA in the GCG Wisconsin Software Package), or by visual inspection (see generally, Current Protocols in Molecular Biology, F. M. Ausubel et al., eds., Current Protocols, a joint venture between Greene Publishing Associates, Inc. and John Wiley & Sons, Inc., (1995 Supplement) (Ausubel)). Additionally, determination of sequence alignment and percent sequence identity can employ the BESTFIT or GAP programs in the GCG Wisconsin Software package (Accelrys, Madison WI), using default parameters provided.

"Derived from" as used herein in the context of enzymes, identifies the originating enzyme, and/or the gene encoding such enzyme, upon which the enzyme was based. For example, the enzyme having the amino acid of SEQ ID NO: 1 was obtained by artificially evolving, over multiple generations the gene encoding a wild-type hydroxylase enzyme in the genomic sequence of the Fo1576 strain of *Fusarium oxysporum* (hereinafter, "FoPipH"). Thus, this evolved FoPip4H enzyme is "derived from" the wild-type FoPip4H enzyme.

"Reference sequence" refers to a defined sequence used as a basis for a sequence comparison. A reference sequence may be a subset of a larger sequence, for example, a segment of a full-length gene or polypeptide sequence. Generally, a reference sequence is at least 20 nucleotide or amino acid residues in length, at least 25 residues in length, at least 50 residues in length, or the full length of the nucleic acid or polypeptide. Since two polynucleotides or polypeptides may each (1) comprise a sequence (i.e., a portion of the complete sequence) that is similar between the two sequences, and (2) may further comprise a sequence that is divergent between the two sequences, sequence comparisons between two (or more) polynucleotides or polypeptide are typically performed by comparing sequences of the two polynucleotides over a "comparison window" to identify and compare local regions of sequence similarity.

"Lewis acid" means a compound that can accept a pair of electrons.

"Reducing agent" means a substance that results in reduction of other substances. The change in oxidation state occurs by having the substance itself be oxidized. Examples of reducing agents include $H_2$ (i.e., molecular hydrogen), secondary alcohols (e.g., isopropanol).

Methods of Preparing of Preparing Belzutifan and Intermediates of Belzutifan

A process for preparing belzutifan of the present disclosure is described in the following Schemes and Examples. Starting materials and intermediates are purchased, made from known procedures, or as otherwise illustrated.

Scheme 1

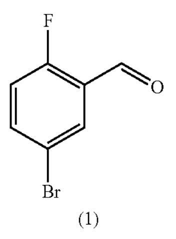

(1)

+

-continued

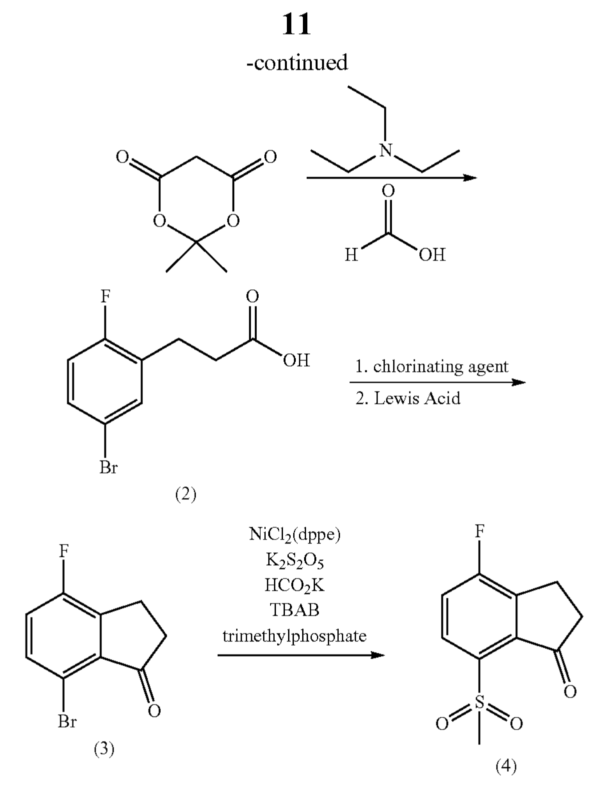

(2)

(3)

(4)

As shown above in Scheme 1, phenylpropionic acid (2) is prepared by reacting benzaldehyde (1) with Meldrum's acid in the presence of a trialkylamine, e.g. triethyl amine, and an acid, e.g. formic acid. Phenylpropionic acid (2) is then cyclized by treating it with a chlorinating agent, e.g. thionyl chloride, followed by treatment with a Lewis Acid e.g. aluminum trichloride, to provide the bromo indanone intermediate (3). Bromo indanone (3) is then converted to indanone (4) using a nickel-catalyzed sulfonylation process.

Scheme 2

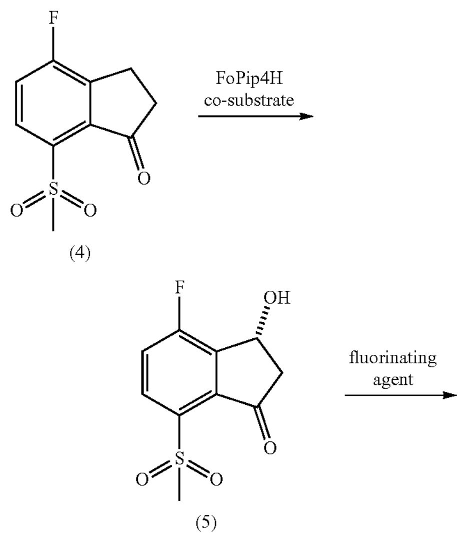

(4)

(5)

-continued

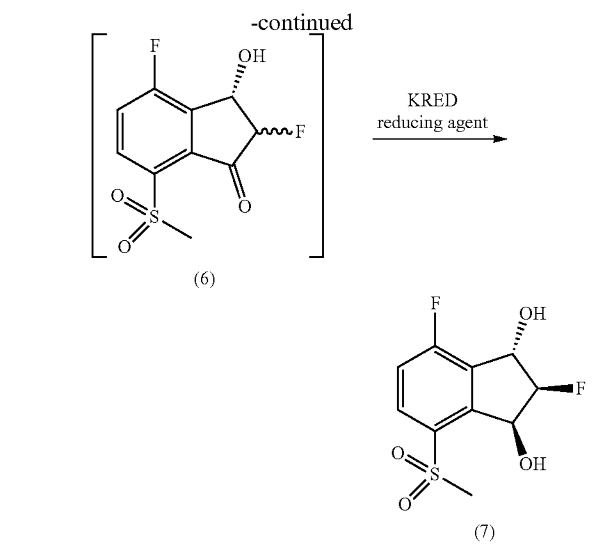

(6)

(7)

As shown above in Scheme 2, in Step 4 indanone (4) is contacted with the enzyme FoPip4H and a co-substrate to provide the hydroxy indanone (5). FoPip4H is an enzyme whose sequence was originally derived from the genomic sequence of a strain of *Fusarium oxysporum.*

Typically, the co-substrate is α-ketoglutarate. In some embodiments, the reaction mixture is buffered at pH from 6-7 using, e.g., a phosphate buffer, and a reducing agent such as L-cysteine is typically included. Alternative buffering agents include Bis Tris (2-bis(2-hydroxyethyl)amino-2-(hydroxymethyl)-1,3-propanediol), PIPES (piperazine-N,N-bis (2-ethanesulfonic acid), citrate, bicine ([bis(2-hydroxyethyl) amino]acetic acid), and TEOA (triethanolamine). Alternative reducing agents include ascorbic acid and dithiothreitol. Mohr's Salt ($(NH_4)_2Fe(SO_4)_2$ $6H_2O$) can be advantageously included as a source of $Fe^{2+}$ ions, which the reducing agent, e.g., L-cysteine, assists in maintaining in the $Fe^{2+}$ state. Other ferrous salts such iron(II) chloride can also serve as a source $Fe^{2+}$. Although the FoPip4H enzyme binds $Fe^{2+}$ and uses it catalytically, the Applicant has observed that adding Mohr's salt and the reducing agent to the reaction mixture provides higher conversions.

In certain embodiments, the reaction mixture includes an aqueous co-solvent system comprising an organic solvent (e.g., ethanol, isopropanol, dimethyl sulfoxide, dimethylformamide, ethyl acetate, butyl acetate, 1-octanol, heptane, octane, methyl t-butyl ether, toluene, and the like), ionic or polar solvents (e.g., 1-ethyl 4 methylimidazolium tetrafluoroborate, 1-butyl-3-methylimidazolium tetrafluoroborate, 1-butyl 3 methylimidazolium hexafluorophosphate, glycerol, polyethylene glycol, and the like). In a specific embodiment, the process using the FoPip4H polypeptide is performed in a co-solvent system of water and 1-octanol.

In some embodiments the FoPip4H enzyme comprises an amino acid sequence having at least a 90% sequence identity to SEQ ID NO: 1. SEQ ID NO:1 has the following amino acid sequence:

(SEQ ID NO: 1)

MGSHHHHHHHHGSAALNADTLDMSLFFGTPSQKQDFCDSLLRLLKARGVV

KLINHPIPSESIHELFAQTKRFFNLPLETKMLAKHPEQALPARGYAFVGQ

ENVANISGYEKGLPPLKTRDIKETVDFGSANDEKYDNLWVPEEELPGFRS

-continued

FMEGFYELAFKTEMQILEALAIALGVSPDHLKSLHNRAHSELRILHYPAI

PASELADGTATRIAEHTDFGSITMLFQDGVGGLQVEDQENLGTFNNVESA

SPTDIILNIGDSLQRLTNDTFKAACHRVTWPPSIKDGDGSEVIPERYSVA

YFVKPNRSASLFPLKEFIEEGVPPKYEDLTFEEWNNRRIEKLFSAEAKA.

In certain embodiments, the FoPip4H enzyme comprises an amino acid sequence having at least a 95% sequence identity to SEQ ID NO: 1. In specific embodiments, the FoPip4H enzyme comprises the amino acid sequence identical to SEQ ID NO: 1.

Conversion of the hydroxy indanone (5) to fluorodiol (7) can be conveniently conducted using a one-reactor vessel process. Hydroxy indanone (5) is contacted with a fluorinating agent under acidic conditions to yield fluoro hydroxyindanone (6). Suitable acids to include in the reaction mixture include acids such as methane sulfonic acid, camphor sulfonic acid, sulfuric acid and other mineral acids in catalytic amount, such as 0.1 to 0.5 equiv, e.g. 0.2 equivalents. Suitable fluorinating agents include 1-chloromethyl-4-fluoro-1,4-diazoniabicyclo[2.2.2]octane bis(tetrafluoroborate) (Selectfluor™), 1-fluoropyridinium tetrafluoroborate, N-fluorobenzenesulfonamide, 1-fluoro-2,4,6-trimethylpyridinium tetrafluoroborate, 2,6-dichloro-1-fluoropyridinium tetrafluoroborate, 2-fluoro-3,3-dimethyl-2,3-dihydro-1,2-benzisothiazole 1,1-dioxide, 4-iodotoluene difluoride, and xenon difluoride. In certain embodiments, the fluorinating agent is 1-chloromethyl-4-fluoro-1,4-diazoniabicyclo[2.2.2]octane bis(tetrafluoroborate) ((Selectfluor™). The fluorination step is typically performed in a mixture of a dipolar aprotic solvent, e.g. acetonitrile, and an alcohol solvent, e.g. methanol. In some embodiments, 1,3-dimethoxybenzene is added to stop the reaction after conversion to the intermediate (6). In some preferred embodiments, a diketone or keto(di)ester, e.g., methylacetoacetate is used to quench the reaction. Such reagents quench formaldehyde which results from the fluorination reaction and thereby minimizes the production of impurities.

Fluoro hydroxyindanone (6) is converted to fluorodiol (7) by an enzyme-catalyzed, stereoselective conversion using a ketoreductase (KRED) enzyme. In some embodiments, intermediate (6) is contacted with the ketoreductase in the same reaction vessel where the fluorination step occurs. Preferably, a cofactor that operates in combination with the ketoreductase enzyme is included. As used herein, the term "cofactor" refers to a non-protein compound that operates in combination with the ketoreductase enzyme. Cofactors suitable for use in the process of the present disclosure include NADP+, NADPH, NAD+, and NADH. In some embodiments NADP+ is added to the enzyme-containing reaction mixture.

Typically, a secondary alcohol, such as 2-propanol is added as a reducing agent that reduces the oxidized form of the cofactor to the reduced form. Other suitable secondary alcohols include 2-butanol, 2-pentanol, and 2-hexanol.

In some embodiments the ketoreductase comprises an amino acid sequence having at least 90% sequence identity to SEQ ID NO: 2. SEQ ID NO:2 has the following amino acid sequence:

(SEQ ID NO: 2)

MKKIDNAVLPAGSLVLVTGANGFVGSHVVEQLLEHGYKVRGTARSASKLA

NLQKRWDAKYPGRFETAVVEDMLKDGAYDEVIKGAAGVAHIASPVSFSPK

-continued

YDEVVPPAIGGTLNALRAAAATPSVKRFVLTSSMMAAIVPKPNVPGIYLD

EKSWNLESIDKAVTLPESHKEKGLWVYAASKTMAEMLAWHFMDENKPHFT

LNTVLPAYTIGTIFDPETQSGSTSGIVMKLFNGEVSPMLALFGPQHYVSA

FDIGLLHLGCLVLPQIERRRVYGTAAPFDWNMVLAVFRKLWPSKTFPADF

PDQGQDLSVFDTRPSLEILKSLGREGWRSFEDSIKDLVGSEFDGQTGHHH

HHH.

In certain embodiments, the ketoreductase comprises an amino acid sequence having at least a 95% sequence identity to SEQ ID NO: 2. In specific embodiments, the ketoreductase comprises the amino acid sequence identical to SEQ ID NO: 2.

Scheme 3

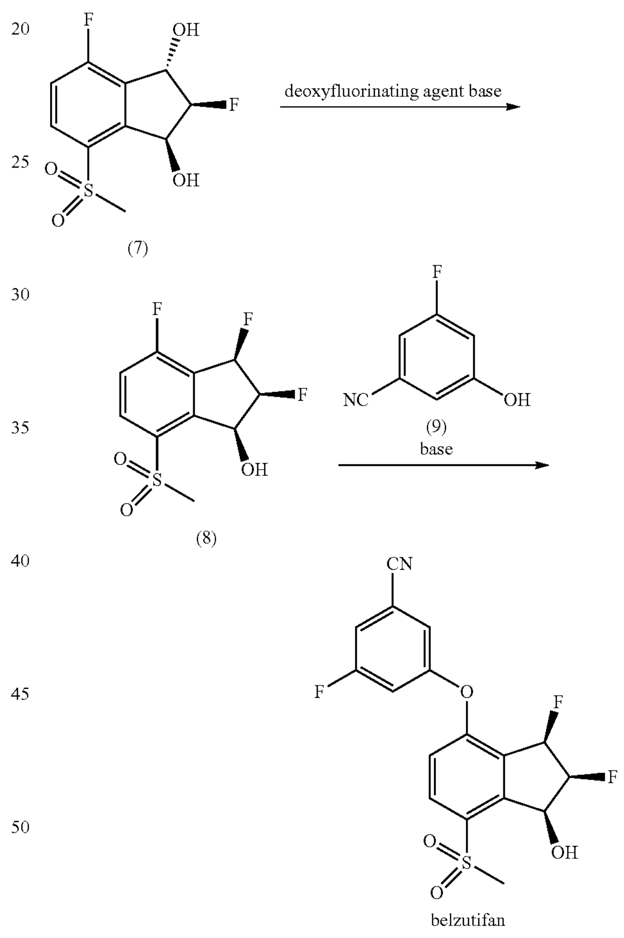

(7)
(8)
(9)
belzutifan

Scheme 3 shows the final steps in the conversion to belzutifan. Fluoro diol (7) is treated with a deoxyfluorinating agent and a base to provide trifluoro indanol (8). Suitable deoxyfluorinating agents for this step include 1,1,2,2,3,3,4,4,4-nonafluorobutane-1-sulfonyl fluoride, bis(2-methoxyethyl)aminosulfur trifluoride (Deoxo-Fluor®), 2-pyridinesulfonyl fluoride (PyFluor), sulfur tetrafluoride, morpholinosulfur trifluoride, xtalfluor-E, xtalfluor-M, and diethylaminosulfur trifluoride (DAST). In a specific embodiment, the deoxyfluorinating agent is 1,1,2,2,3,3,4,4,4-nonafluorobutane-1-sulfonyl fluoride. Suitable bases for this step include trialkylamine bases such as triethylamine.

Trifluoro indanol (8) is coupled with phenol (9) to provide belzutifan. Typically, the coupling is performed in an aqueous solution in the presence of a base, which is sufficient under the reaction conditions to deprotonate the phenolic hydrogen under the action conditions. Suitable bases for this reaction include but are not limited to organic bases such as dialkylamine bases, trialkylamine bases, aromatic amine bases, and inorganic bases, such as carbonate, bicarbonate, phosphate and borate bases. In alternative embodiments, the phenoxide of the phenol (9) is employed directly in the coupling step. For example, lithium, sodium, potassium, cesium salts of the phenol (9) can be isolated and then used in the coupling step without added base.

In some embodiments, phenol (9) is prepared by treating 3,5-difluorobenzonitrile with potassium t-butoxide and 2-phenylethanol.

In specific embodiments, the isolation of belzutifan further comprises treating belzutifan with activated carbon; recrystallizing the decolorized belzutifan from a mixture of a alcohol solvent and water; and isolating purified belzutifan. The decolorization of belzutifan is typically conducted in a dipolar aprotic solvent, e.g., acetonitrile. The recrystallization is typically conducted by addition of an antisolvent, e.g., water, to the dipolar aprotic solvent.

Throughout the synthetic schemes and examples below, abbreviations and acronyms may be used with the following meanings unless otherwise indicated:

D.I.=deionized; DME=1,2-dimethoxyethane; DMF=N,N-dimethylformamide; EDTA=ethylenediaminetetraacetic acid; FA=formic acid; hIPA=isopropanol; KF=Karl Fischer analysis; α-KG=α-ketoglutarate; KRED=ketoreductase enzyme; KOtBu=potassium tert-butoxide; MeCN=acetonitrile; MeOH=methanol; MsOH=methanesulfonic acid; NMP=N-methyl-2-pyrrolidone; RT=room temperature; catalyst; TBAB=tetrabutylammonium bromide; SELECTFLUOR=-chloromethyl-4-fluoro-1,4-diazoniabicyclo[2.2.2]octane bis (tetrafluoroborate); TEA=triethylamine; THF=tetrahydrofuran; TsOH=p-toluenesulfonic acid; V=volume(s).

Examples

The compounds and crystalline forms thereof described herein can be prepared according to the procedures of the following schemes and examples, using appropriate materials and are further exemplified by the following specific examples. The examples further illustrate details for the preparation of the compounds and crystalline forms of the present disclosure. Those skilled in the art will readily understand that known variations of the conditions and processes of the following preparative procedures can be used to prepare these compounds and their crystalline forms. These examples are provided for the purpose of further illustration only and are not intended to be limitations on the disclosure.

Concentration refers to the removal of the volatile components at reduced pressure (e.g., by rotary evaporation) unless otherwise noted. All temperatures are in degrees Celsius unless otherwise noted. $^1$H NMR spectra were recorded at 600 MHz at ambient temperature unless otherwise noted. NMR samples were dissolved in in $CDCl_3$, DMSO-$d_6$, or Methanol-$d_4$ with the chemical shifts reported relative to tetramethylsilane standard. Resonance signals are reported by the following abbreviations: s=singlet, d=doublet, t=triplet, q=quartet, dd=doublet of doublets, m=multiplet or overlap of nonequivalent resonances. Coupling constants (J) are reported in Hertz (Hz).

Step 1: Preparation of 3-(5-bromo-2-fluorophenyl)propanoic Acid (2)

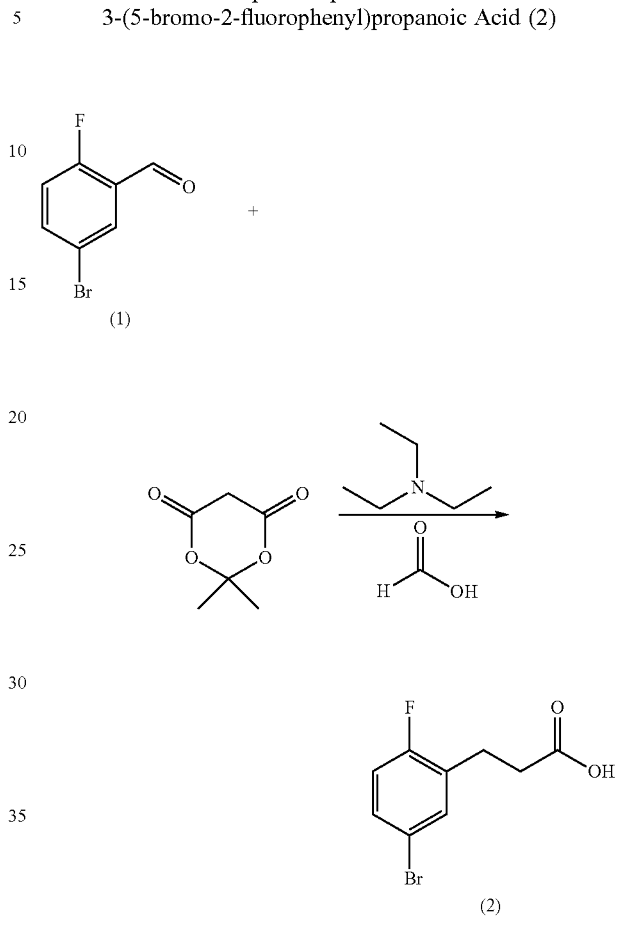

Under nitrogen, triethylamine (13.1 L, 93.6 mol) and formic acid (7.21 L, 187 mol) was combined at less than 10° C. The stirred batch was charged with 5-bromo-2-fluorobenzaldehyde (1) (8.00 kg, 95 wt %, 37.4 mol) at less than 10° C., followed by 2,2-dimethyl-1,3-dioxane-4,6-dione (6.04 kg, 98 wt %, 41.2 mol) at less than 20° C. The reaction was stirred at 55±10° C. for 1-2 h and at 95-100° C. for 8-12 h. The batch was cooled to 15-30° C. and then slowly charged 6 N hydrogen chloride (7.80 L, 46.8 mol) at 20-30° C. and added seed (2) (40 g). The batch was stirred at 20-30° C. to form slurry and slowly charged another portion 6 N hydrogen chloride (7.80 L, 46.8 mol) at 20-30° C., followed by addition of water (19.0 L) at 20-30° C. The slurry batch was slowly cooled to 15-20° C. and stirred at 15-20° C. for 2-3 h. Solids were filtered, washed with water (11.4 L×2), then dried under vacuum at 20-30° C. for 24 h to afford (2) (8.74 kg, 94% yield). $^1$H NMR (599.90 MHz, DMSO-$d_6$) δ 7.52 (dd, J=6.7 and 2.6 Hz, 1H, CH), 7.43 (ddd, J=8.7, 4.6 and 2.6 Hz, 1H, CH), 7.14 (dd, J=9.9 and 8.7 Hz, 1H, CH), 2.82 (t, J=7.6 Hz, 2H, CH2), 2.54 (t, J=7.4 Hz, 2H, CH2) ppm. $^{13}C\{^1H\}$ NMR (150.85 MHz, DMSO-$d_6$) δ 173.24 (s, COOH), 159.65 (d, $J_{CF}$=244.1 Hz, CF), 133.10 (d, $J_{CF}$=5.0 Hz, CH), 130.77 (d, $J_{CF}$=8.4 Hz, CH), 130.18 (d, $J_{CF}$=17.2 Hz, C), 117.35 (d, $J_{CF}$=23.8 Hz, CH), 115.89 (d, $J_{CF}$=3.0 Hz, C), 33.29 (s, CH2), 23.35 (d, $J_{CF}$=2.3 Hz, CH2) ppm. $^{19}$F NMR (564.47 MHz, DMSO-$d_6$) δ −120.94 (m, 1F) ppm.

Step 2: Preparation of 7-bromo-4-fluoro-2,3-dihydro-1H-inden-1-one (3)

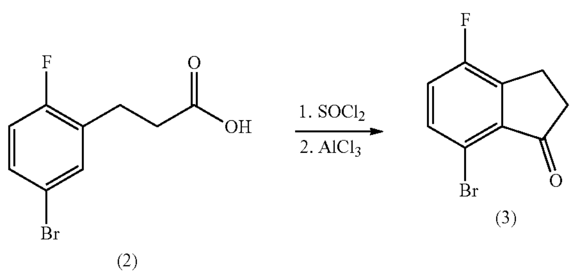 [SMILES: O=C(O)CCc1cc(Br)ccc1F ; O=C1CCc2c(F)ccc(Br)c21]

(2) (3)

Thionyl chloride (12.00 L) was charged to a vessel under nitrogen, equipped with a NaOH scrubber, followed by (2) 3-(5-bromo-2-fluorophenyl)propanoic acid (4.00 kg) and stirred at 15-20° C. for 2 h. The batch was cooled to −5° C. to −10° C. and aluminum chloride (3.24 kg) was charged portionwise, maintaining the batch temperature between 0-10° C. The batch was warmed to 20-25° C. over 2-3 h and aged at 25-30° C. for 16 h. After completion, the batch was cooled to 20-25° C. and quenched by slowly transferring the solution to a separate vessel containing 0.5 N HCl (40.0 L), equipped with a NaOH scrubber, while maintaining a batch temperature of 0-10° C. Toluene (40.0 L) was then charged to the vessel, agitated, and the bottom aqueous layer discarded. The organic solution was washed with 0.5 N HCl (8.0 L), followed by D.I. water (8.0 L) and 10% aq $NaHCO_3$ (2×20.0 L). The toluene solution was then distilled under reduced pressure to~3 vol, followed by a constant volume solvent switch to 2-propanol (40.0 L, 10 vols), maintaining a volume of ~20.0 L. The heterogeneous mixture was then heated to 75-80° C. to dissolve the solids, cooled to 70-75° C., and then seeded (40 g). The batch was aged for 1 h then cooled to 5-10° C. over 6 h and then filtered. The solids were washed with cold (5° C.) 2-propanol (2×4.0 L) and dried under vacuum at 20-25° C. to afford (3) (3.24 kg, 83%) as an off white solid. $^1H$ NMR (599.90 MHz, DMSO-$d_6$) δ 7.61 (dd, J=8.5 and 4.3 Hz, 1H, CH), 7.43 (t, J=8.5 Hz, 1H, CH), 3.04 (m, 2H, CH2), 2.71 (m, 2H, CH2) ppm. $^{13}C\{^1H\}$ NMR (150.85 MHz, DMSO-$d_6$) δ 202.36 (s, C═O), 158.93 (d, $J_{CF}$=247.8 Hz, CF), 143.99 (d, $J_{CF}$=21.3 Hz, C), 135.84 (d, $J_{CF}$=4.9 Hz, C), 133.72 (d, $J_{CF}$=6.5 Hz, CH), 121.89 (d, $J_{CF}$=21.6 Hz, CH), 112.42 (d, $J_{CF}$=3.3 Hz, C), 36.42 (s, CH2), 20.30 (s, CH2) ppm. $^{19}F$ NMR (564.47 MHz, DMSO-$d_6$) δ −121.80 (dd, $J_{HF}$=8.5 and 4.3 Hz, 1F) ppm.

Step 3: Preparation of 4-fluoro-7-(methylsulfonyl)-2,3-dihydro-1H-inden-1-one (4)

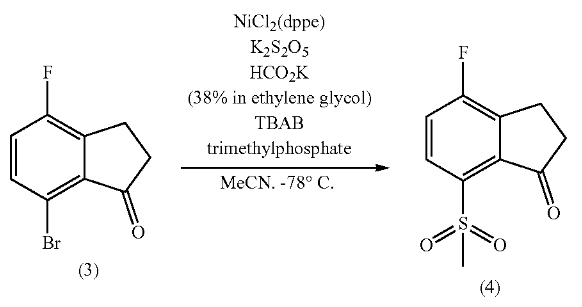

(3) (4)

Potassium formate (17.5 g, 208 mol, 1.6 equiv) and ethylene glycol (25.0 mL) were combined in vessel A and stirred at 40° C. until homogeneous, whereupon the solution was cooled to ambient temperature. In a separate vessel (vessel B), 7-bromo-4-fluoro-2,3-dihydro-1H-inden-1-one (3) (30.0 g, 130 mol, 1.0 equiv), potassium metabisulfite (37.5 g, 169 mol, 1.3 equiv), $NiCl_2$-dppe (3.43 g, 6.49 mmol, 5 mol %), tetrabutylammonium bromide (29.3 g, 91 mmol, 0.7 equiv), and acetonitrile (300 mL) were combined. The suspension was degassed via $N_2$ sparge for 1 h. Trimethylphosphate (45.5 g, 325 mmol, 2.5 equiv) and a portion of solution from vessel A (2.1 mL) were charged. The mixture was heated to 78° C. ($T_i$) and stirred for 1 h, whereupon the remaining vessel A solution (31.3 mL) was charged over 24 h via syringe pump. Upon completion of the addition, the reaction was stirred for 12 h at 78° C. and was then cooled to 25° C. Toluene (300 mL) and 1 N HCl (300 mL) were charged to the vessel, and the mixture was stirred for 1 h at 25° C. The layers were separated and the aqueous layer was extracted with toluene/acetonitrile (1:1, 150 mL). The organic layers were combined and concentrated to 240 mL, whereupon 2-propanol (390 mL) was added under constant distillation maintaining a volume of 240 mL. The resulting slurry was aged for 12 h, filtered, and dried to afford (4) (22.3 g, 75%) as a white solid: $^1H$ NMR (599.90 MHz, DMSO-$d_6$) δ 8.02 (dd, J=8.4 and 4.6 Hz, 1H, CH), 7.74 (t, J=8.4 Hz, 1H, CH), 3.41 (s, 3H, CH3), 3.17 (m, 2H, CH2), 2.82 (m, 2H, CH2) ppm. $^{13}C\{^1H\}$ NMR (150.85 MHz, DMSO-$d_6$) δ 202.50 (s, C═O), 162.47 (d, $J_{CF}$=255.8 Hz, CF), 144.75 (d, $J_{CF}$=21.6 Hz, C), 136.71 (d, $J_{CF}$=6.0 Hz, C), 133.80 (d, $J_{CF}$=3.7 Hz, C), 130.52 (d, $J_{CF}$=8.1 Hz, CH), 120.19 (d, $J_{CF}$=20.8 Hz, CH), 42.67 (s, CH3), 36.29 (s, CH2), 21.42 (s, CH2) ppm. $^{19}F$ NMR (564.47 MHz, DMSO-$d_6$) δ −112.12 (dd, $J_{HF}$=8.4 and 4.6 Hz, 1F) ppm.

Step 4: Preparation of (R)-4-fluoro-3-hydroxy-7-(methylsulfonyl)-2,3-dihydro-1H-inden-1-one (5)

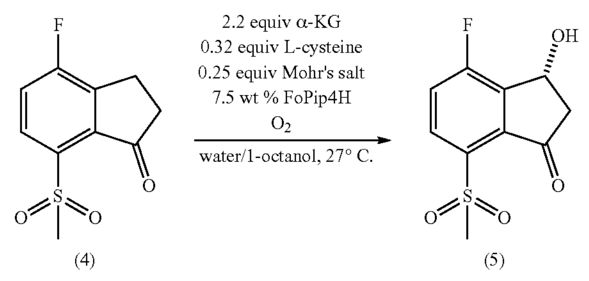 [SMILES: CS(=O)(=O)c1ccc(F)c2c1C(=O)CC2 ; CS(=O)(=O)c1ccc(F)c2c1C(=O)C[C@H]2O]

(4) (5)

Water (34.5 L, 23 vol.) was added to a 100 L reactor and adjusted to 20-30° C. Following addition of alpha-ketoglutaric acid (2.11 kg, 14.46 mol, 2.20 equiv.), the solution was sparged with $N_2$ until dissolved oxygen (dO) level was <2%. L-cysteine (0.26 kg, 2.10 mol, 0.32 equiv.) was added, and pH was adjusted to 6.8 with 10 N NaOH. Mohr's salt (0.64 kg, 1.64 mol, 0.25 equiv.) was added, followed by 5 N NaOH to adjust to pH 6.0. 1-octanol (1.13 L, 0.75 vol) was added, followed by lyophilized fermentation powder containing FoPip4H (0.11 kg, 7.5 wt %) and then sulfone (4) (1.5 kg, 6.57 mol, 1.00 equiv.). The reaction dO level was brought to 100%, and the suspension was stirred for 24 to 48 h, after which sulfuric acid was added to adjust to pH 4.7. To this mixture was added $(NH_4)_2(SO_4)$ (9.0 kg, 68.1 mol) and 50% MeCN in toluene (42 L, 28 vol.) followed by CELITE (3.0 kg) and the mixture heated to 45° C. for 2 h, then cooled to 25° C. The mixture was filtered and the organic layer was separated. The filtered cake was washed with 25% MeCN in toluene (15 L, 10 vol.) twice. The aqueous layer was back-extracted with the cake wash solvent twice and the organic layers combined and washed with water (1.1 L, 0.75 vol). The organic layer was concentrated to 10 vol. at 50° C. under vacuum then stirred for 2 h at 55° C., cooled to 25° C. over 4 h and stirred for an additional 10 hrs. The slurry was filtered and washed with 5% MeCN in toluene (1.5 L, 1 vol.) three times. The cake was dried under vacuum to afford 1.39 kg of hydroxysulfone (5) (99 wt %, 5.63 mol, 86% yield). $^{1}H$ NMR (599.90 MHz, DMSO-$d_6$) δ 8.11 (dd, J=8.4 and 4.4 Hz, 1H, CH), 7.78 (t, J=8.5 Hz, 1H, CH), 5.97 (d, J=7.3 Hz, 1H, OH), 5.46 (td, J=7.1 and 2.2 Hz, 1H, CH), 3.42 (s, 3H, CH3), 3.20 (dd, J=18.8 and 6.8 Hz, 1H, CH'H"), 2.59 (dd, J=18.8 and 2.2 Hz, 1H, CH'H") ppm. $^{13}C\{^{1}H\}$ NMR (150.85 MHz, DMSO-$d_6$) δ 200.17 (s, C═O), 162.85 (d, $J_{CF}$=259.9 Hz, CF), 145.05 (d, $J_{CF}$=19.2 Hz, C), 136.02 (d, $J_{CF}$=5.1 Hz, C), 133.24 (d, $J_{CF}$=4.0 Hz, C), 132.32 (d, $J_{CF}$=8.5 Hz, CH), 121.39 (d, $J_{CF}$=21.0 Hz, CH), 63.85 (s, CH), 47.22 (s, CH2), 42.65 (s, CH3) ppm. $^{19}F$ NMR (564.47 MHz, DMSO-$d_6$) δ −110.86 (dd, $J_{HF}$=8.6 and 4.5 Hz, 1F) ppm.

Step 5: Preparation of (1S,2R,3S)-2,4-difluoro-7-(methylsulfonyl)-2,3-dihydro-1H-indene-1,3-diol (7)

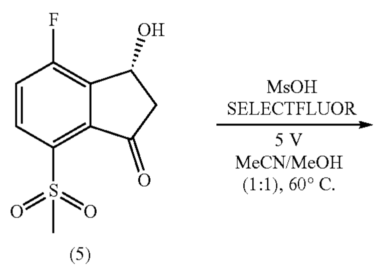

(5)

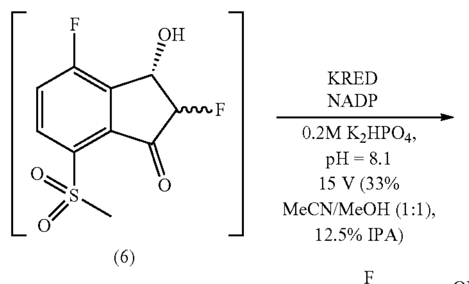

(6)

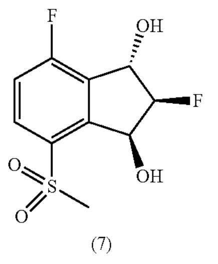

(7)

Acetonitrile (2.5 L), methanol (2.5 L), (5) (1.0 kg, 1.0 equiv), methane sulfonic acid (118 g, 0.3 equiv), and SELECTFLUOR (1.596 kg, 1.1 equiv) were charged to a five-gallon Hastelloy C-276 reactor. The vessel was pressure purged with $N_2$ a total of five times, and then the resulting mixture was agitated and heated to 60° C. for 16 h. Methyl acetoacetate (95 g, 0.2 equiv) and water (369 g, 5 equiv) were charged and the batch was further aged at 60° C. for 2 h. The batch was then cooled to 20° C. and 0.2 M $K_2HPO_4$ (7.75 L) was added. 50 wt % NaOH (344 g, 1.05 equiv) was added over 15 min to neutralize the acidic solution (final pH=6.3). This mixture was agitated and then transferred into high density polyethylene carboys. The reaction mixture was then vacuum transferred into a 30 L glass reactor. Isopropanol (2.25 L) was added to the reaction followed by a solution containing KRED and NADP (1.5 L 0.2 M $K_2HPO_4$ containing 40 g KRED and 15 g NADP). The solution pH was adjusted by adding 5 N NaOH (288 g, 0.3 equiv) over 25 minutes (final pH=8.1). The solution was agitated and heated to 34° C. for 17 h. The reaction volume was reduced to 10 L via batch concentration. When the batch volume reached 10 L, D.I. $H_2O$ (1 L) was added and the batch was concentrated to 10 L total volume. $K_2CO_3$-treated CELITE (44 g, 0.044 w/w) and $(NH_4)_2SO_4$ (5.8 kg, 5.8 w/w) were charged to the reactor and the batch was agitated and heated to 50° C. for 2 h. EtOAc (15 L) was charged at 50° C. and mixed for 30 min. The reaction was then cooled to 20° C. and aged for 30 min. The slurry was filtered through a 2' filter pot lined with polypropylene and filter paper and the waste cake was washed with EtOAc (2×5 L). The filtrates were combined in a 50 L glass reactor and the aqueous phase was drained and discarded. The organic layer was sequentially washed with 40% (w/w) $(NH_4)_2SO_4$ (2×4 L), 25% (w/w) $K_2HPO_4$ (2 L) and 50% (w/w) $K_2HPO_4$ (2 L). The resulting organics were concentrated to 15 L and distilled at constant volume via addition of fresh EtOAc until <0.3 wt % water. The batch was transferred to a 50 L round bottom flask, CUNO #5 (130 g, 0.13 w/w) was added and the mixture was agitated under ambient conditions for 30 min. The slurry was filtered through a 10" filter pot lined with polypropylene and filter paper and the filter cake was washed with EtOAc (2×2 L). The filtrate was transferred into a 20 L glass vessel and concentrated to 10 L at 60° C., then cooled to 30° C., and seeded with (6) (10 g, 0.01 w/w). The resulting slurry was aged at 30° C. for 1 h, followed by addition of toluene (8.5 L) over 4 h and further aging for 9 h. The mixture was concentrated to 6 L, then distilled at constant volume via addition of fresh toluene (2 L). The slurry was cooled 20° C. over 30 min, aged for 1 h, and filtered. The product cake was washed with 1:4 EtOAc/toluene (2 L) and toluene (2 L), and then dried in a vacuum oven at 40° C. to give (6) as an off-white solid (950 g, 85% yield, 96.7 area % by LC, 96.3 wt %). $^{1}H$ NMR (599.90 MHz, DMSO-$d_6$) δ 7.92 (ddd, J=8.6, 4.7 and 0.7 Hz, 1H, CH), 7.46 (t, J=8.9 Hz, 1H, CH), 6.14 (d, J=7.1 Hz, 1H, OH), 5.96 (d, J=6.9 Hz, 1H, OH), 5.56 (dd, J=6.8, 5.2 and 3.2 Hz, 1H, CH), 5.40 (ddd, J=14.1, 7.0 and Hz, 1H, CH), 4.89 (dt, J=51.1 and 5.2 Hz, 1H, CH), 3.31 (s, 3H, CH3) ppm. $^{13}C\{^{1}H\}$ NMR (150.85 MHz, DMSO-$d_6$) δ 162.31 (d, $J_{CF}$=258.7 Hz, CF), 142.85 (dd, $J_{CF}$=6.0 and 2.9 Hz, C), 133.89 (d, $J_{CF}$=3.4 Hz, C), 132.20 (d, $J_{CF}$=8.9 Hz, C), 130.53 (dd, $J_{CF}$=16.4 and 10.1 Hz, CH), 117.25 (d, $J_{CF}$=21.4 Hz, CH), 97.82 (d, $J_{CF}$=194.0 Hz, CH), 73.17 (d, $J_{CF}$=25.2 Hz, CH), 68.95 (d, $J_{CF}$=17.9 Hz, CH), 44.93 (s, CH3) ppm. $^{19}F$ NMR (564.47 MHz, DMSO-$d_6$) δ −111.51 (dd, $J_{HF}$=9.9 and 4.6 Hz, 1F), −203.88 (dd, $J_{HF}$=51.0 and 13.9 Hz, 1F) ppm.

Step 6: Preparation of (1S,2S,3R)-2,3,4-trifluoro-7-(methylsulfonyl)-2,3-dihydro-1H-inden-1-ol (8)

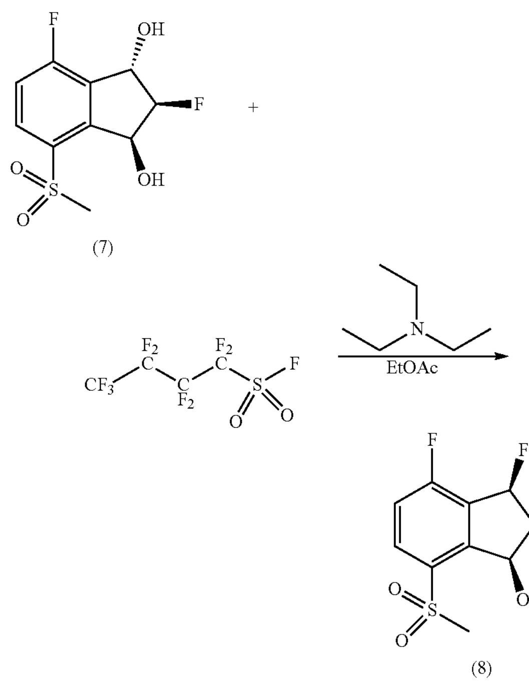

(7)

(8)

Under nitrogen, (1S,2R,3S)-2,4-difluoro-7-(methylsulfonyl)-2,3-dihydro-1H-indene-1,3-diol (7) (631.6 g, 95 wt %, 2.271 mol) and ethyl acetate (6.00 L) were combined. The stirred batch was cooled to −15° C. and then charged triethylamine (731.7 mL, 5.223 mol) at less than −10° C., followed by 1,1,2,2,3,3,4,4,4-nonafluorobutane-1-sulfonyl fluoride (492.5 g, 2.725 mol) at −15 to −10° C. The batch was stirred at −15 to −10° C. for 2-3 h and at 0-5° C. for 20-24 h. The batch was charged with 35% potassium carbonate solution (1.80 L) at less than 20° C. and then 2 N potassium hydroxide (1.87 L) at less than 20° C. The batch was stirred at 10-20° C. for 0.5 h then the phases separated. The organic layer was charged with 35% potassium carbonate solution (0.90 L) at less than 20° C. and then 2 N potassium hydroxide (0.94 L) at less than 20° C. The batch was stirred at 10-20° C. for 0.5 h then the phases separated. The organic layer was charged with 35% potassium carbonate solution (1.20 L) at less than 20° C. The batch was stirred at 10-20° C. for 0.5 h then the phases separated. The organic layer was azeotropically dried with ethyl acetate to KF≤250 ppm and adjusted to a total volume (4.5 L). The batch was slowly charged with toluene (3.0 L) at 15-25° C. and stirred at 15-25° C. for 4 h. Solids were filtered, washed with 1:1 ethyl acetate/toluene (0.90 L×2). The combined filtrates were treated with activated carbon CUNO #5 (120 g) at 20-30° C. for 2 h. Solids were filtered, washed with ethyl acetate (1.2 L×3). The combined filtrates were concentrated and solvent-switched to isopropanol (2.4 L, total volume) at 30-40° C. and seed. The batch was slowly charged with heptane (0.66 L) at 30-40° C. then slowly cooled to −2 to 3° C. and stirred at −2 to 3° C. for 5 h. Solids were filtered, washed with 60:40 isopropanol/heptane (0.90 L), then dried under vacuum with nitrogen sweep at 20-30° C. for 24 h to afford (8) (528 g, 87% yield). $^1$H NMR (599.90 MHz, DMSO-$d_6$) δ 8.11 (ddd, J=8.7, 4.9 and 1.9 Hz, 1H, CH), 7.62 (td, J=8.7 and 0.7 Hz, 1H, CH), 6.24 (dd, J=6.2 and 0.7 Hz, 1H, OH), 6.08 (ddd, J=56.0, 4.8, and 2.1 Hz, 1H, CH), 5.56 (m, 1H, CH), 5.21 (ddt, J=48.1, 16.0, and 4.9 Hz, 1H, CH), 3.37 (s, 3H, CH3) ppm. $^{13}C\{^1H\}$ NMR (150.85 MHz, DMSO-$d_6$) δ 162.18 (d, $J_{CF}$=259.8 Hz, CF), 144.85 (d, $J_{CF}$=4.5 Hz, C), 135.01 (dd, $J_{CF}$=9.3 and 2.9 Hz, CH), 134.54 (s, C), 125.71 (td, $J_{CF}$=17.8 and 4.1 Hz, C), 117.30 (dd, $J_{CF}$=20.8 and 2.3 Hz, CH), 88.97 (dd, $J_{CF}$=198.8 and 15.5 Hz, CH), 86.00 (dd, $J_{CF}$=188.0 and 16.6 Hz, CH), 69.34 (d, $J_{CF}$=18.4 Hz, CH), 44.87 (s, CH3) ppm. $^{19}$F NMR (564.47 MHz, DMSO-$d_6$) δ −109.25 (br, 1F), −184.40 (ddd, $J_{HF}$=55.9, 16.4 and 6.8 Hz, 1F), −212.69 (dd, $J_{HF}$=47.9 and 7.3 Hz, 1F) ppm.

Step 7: Preparation of 3-fluoro-5-hydroxybenzonitrile (9)

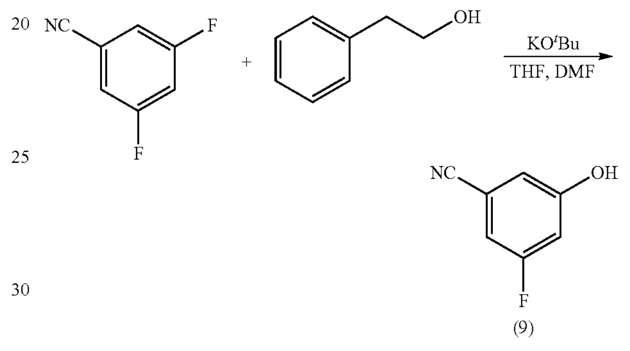

(9)

Under nitrogen, potassium tert-butoxide (8.22 g, 73.3 mmol) and THF (45 mL) were combined into a vessel-1. The stirred batch was charged 2-phenylethan-1-ol (8.60 g, 70.4 mmol) at 25-35° C. and stirred for 10 min to 0.5 h. 3,5-Difluorobenzonitrile (10.0 g, 71.9 mmol) and THF (35 mL) were combined into a vessel-2 at 15-25° C. The mixture was stirred for 0.5 h at 15-25° C. and then was cooled to −3 to 3° C. The solution in vessel-1 was added to the batch in vessel-2 over 5 h while maintaining the batch temperature at −3 to 3° C. The resulting mixture was stirred for 15 g at −3 to 3° C. DMF (16.7 mL, 216 mmol) was added to the batch in vessel-2 at −3 to 5° C. then potassium tert-butoxide (13.7 g, 122 mmol) was added in portions while maintaining the batch temperature below 15° C. The reaction mixture was stirred for 1 h at 0-15° C. and for 15 h at 40-45° C. The reaction mixture was cooled to 0° C. and 30 wt % citric acid (50.6 g, 79 mmol) was added at 0-10° C. Toluene (60 mL) was added and the mixture was stirred for 0.5 h at 20-30° C. The aqueous was separated and the organic layer was washed with 5 wt % lithium chloride (25 mL×2). The resulting organic layer was extracted with 2 N NaOH (41.3 mL, 83 mmol). The aqueous layer was washed with toluene (40 mL×2). The resulting aqueous layer was acidified with 30 wt % citric acid (23.0 g, 35.9 mmol) to pH=5.5-6.3 to form product (9) slurry. Water (50 mL) was slowly added over 2 h while maintaining the batch temperature below 25-35° C. The slurry was cooled to 15° C. Solids were filtered, washed with water (25 mL×2) and 40:60 toluene/heptane (25 mL), then dried under vacuum with nitrogen sweep at 20-30° C. for 24 h to afford (9) (8.64 g, 86% yield). $^1$H NMR (599.90 MHz, DMSO-$d_6$) δ 10.72 (br, 1H, OH), 7.21 (ddd, J=8.5, 2.4, and 1.3 Hz, 1H, CH), 7.02 (m, 1H, CH), 6.93 (dt, J=10.9 and 2.3 Hz, 1H, CH) ppm. $^{13}C\{^1H\}$ NMR (150.85 MHz, DMSO-$d_6$) δ 162.66 (d, $J_{CF}$=245.1 Hz, CF), 159.71 (d, $J_{CF}$=12.4 Hz, C), 117.78 (d, $J_{CF}$=3.9 Hz, C), 115.51 (d, $J_{CF}$=2.8 Hz, CH), 112.91 (d, $J_{CF}$=13.0 Hz, C), 109.67 (d, $J_{CF}$=25.6 Hz, CH), 108.20 (d, $J_{CF}$=23.5 Hz, CH) ppm. 19F NMR (564.47 MHz, DMSO-$d_6$) δ −109.96 (t, $J_{HF}$=9.8 Hz, 1F) ppm.

Step 8: Preparation of Belzutifan

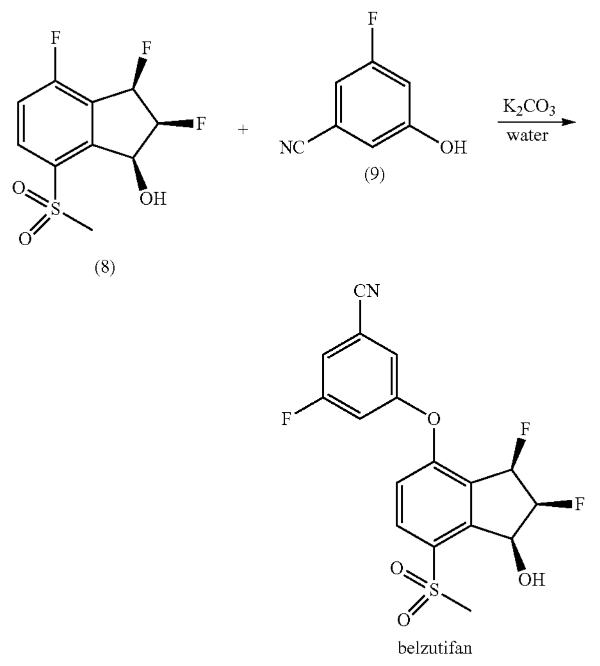

(8)

(9)

belzutifan

To a 1 L reactor with overhead stirring were added (1S,2S,3R)-2,3,4-trifluoro-7-(methylsulfonyl)-2,3-dihydro-1H-inden-1-ol (8) (100 g, 358 mmol), 3-fluoro-5-hydroxy-benzonitrile (9) (73.8 g, 538 mmol), and $K_2CO_3$ (37.2 g, 269 mmol) followed by water (500 mL, 5V). The mixture was stirred for 30 min at rt and then heated to 85° C. over 30 min. Once at 85° C., the reaction stirred for 48 h. After 48 h, the reaction was cooled to 50° C. over 15 min and MeCN (100 mL, 1 V) was added. The reaction stirred for 5 min before cooling down to rt over 30 min and then stirring overnight at rt. The mixture was then filtered and a slurry wash was performed with 40% MeCN/H2O (400 mL, 4 V) two times. The washed cake was then dried under vacuum oven at 50° C. under $N_2$ sweep overnight to afford crude belzutifan as a light green solid (110 g, 80.2% yield). The crude belzutifan (110 g, 96.8 wt %) and acetonitrile (1650 mL, 15 V) were charged to a 2 L vessel with overhead stirring. The mixture was agitated and heated to 50° C. to dissolve the crude belzutifan. The batch was treated with activated carbon CUNO #5 (22 g, 20 wt %) at 50° C. for 3 h. The solids were filtered and washed with acetonitrile twice (440 mL, 4V×2). The combined filtrates were charged to a clean 3 L vessel and concentrated to 9 V (990 mL) at 50° C. The batch was heated to 65° C. and aged for 1 h to redissolve any product that precipitated during the distillation. The batch was cooled to 45° C. over 10 min, seeded with 1 wt % pure belzutifan and aged for 1 h at 45° C. Water (1320 mL, 12 V) was added over 6 h. The batch was cooled to 20° C. over 4 h and aged for at least 6 h. The solids were filtered and two displacement washes were performed with 40:60 acetonitrile:water (220 mL, 2 V×2). The washed cake was then dried in a vacuum oven at 50° C. under $N_2$ sweep overnight to afford pure belzutifan as an off-white solid (98 g, 92.0% yield).

| Sequences |
| --- |
| MGSHHHHHHHHGSAALNADTLDMSLFFGTPSQKQDFCDSLLRLLKARGVV KLINHPIPSESIHELFAQTKRFFNLPLETKMLAKHPEQALPARGYAFVGQ ENVANISGYEKGLPPLKTRDIKETVDFGSANDEKYDNLWVPEEELPGFRS FMEGFYELAFKTEMQILEALAIALGVSPDHLKSLHNRAHSELRILHYPAI PASELADGTATRIAEHTDFGSITMLFQDGVGGLQVEDQENLGTFNNVESA SPTDIILNIGDSLQRLTNDTFKAACHRVTWPPSIKDGDGSEVIPERYSVA YFVKPNRSASLFPLKEFIEEGVPPKYEDLTFEEWNNRRIEKLFSAEAKA (SEQ ID NO: 1). |
| MKKIDNAVLPAGSLVLVTGANGFVGSHVVEQLLEHGYKVRGTARSASKLA NLQKRWDAKYPGRFETAVVEDMLKDGAYDEVIKGAAGVAHIASPVSFSPK YDEVVPPAIGGTLNALRAAAATPSVKRFVLTSSMMAAIVPKPNVPGIYLD EKSWNLESIDKAVTLPESHKEKGLWVYAASKTMAEMLAWHFMDENKPHFT LNTVLPAYTIGTIFDPETQSGSTSGIVMKLFNGEVSPMLALFGPQHYVSA FDIGLLHLGCLVLPQIERRRVYGTAAPFDWNMVLAVFRKLWPSKTFPADF PDQGQDLSVFDTRPSLEILKSLGREGWRSFEDSIKDLVGSEFDGQTGHHH HHH (SEQ ID NO: 2). |

What is claimed is:

1. A process for preparing belzutifan

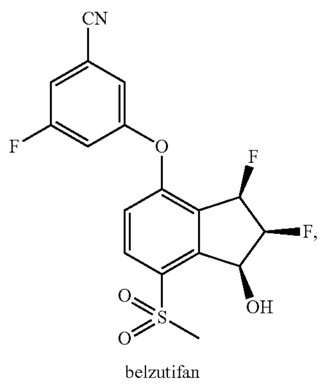 [SMILES: CS(=O)(=O)c1ccc(Oc2cc(F)cc(C#N)c2)c2c1[C@H](O)[C@H](F)[C@@H]2F]

belzutifan comprising:

(a) contacting hydroxy indanone (5)

(5)

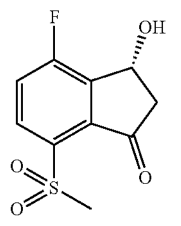

with a fluorinating agent under acidic conditions to yield fluoro hydroxyindanone (6), (6)

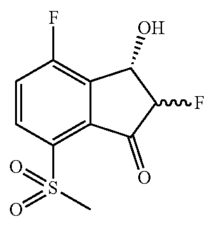

(b) contacting the fluoro hydroxyindanone (6) with a ketoreductase comprising the full-length sequence of SEQ ID NO:2 to provide fluorodiol (7), (7)

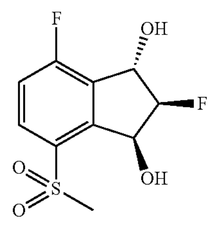

(c) isolating the fluorodiol (7), and (d) converting fluorodiol (7) to belzutifan.

2. The process of claim 1, wherein step (b) further comprises contacting the fluoro hydroxyindanone (6) with NADP.

3. The process of claim 1, wherein the process further comprises preparing the hydroxy indanone (5) of step (a) by contacting indanone (4)

(4)

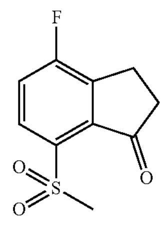

with FoPip4H enzyme comprising the full-length sequence of SEQ ID NO:1 and a co-substrate to provide hydroxy indanone (5).

4. The process of claim 3, wherein the co-substrate is α-ketoglutarate.

5. The process of claim 3, wherein the process further comprises preparing the indanone (4) by contacting bromo indanone (3)

(3)

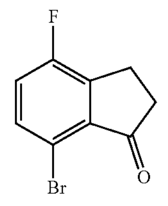

with a metabisulfite salt in the presence of a $Ni^{2+}$ catalyst and a methylating agent to provide the indanone (4).

6. The process of claim 5, wherein the $Ni^{2+}$ catalyst is $NiCl_2$-dppe.

7. The process of claim 5, wherein the methylating agent is selected from the group consisting of trimethyl phosphate, dimethylsulfate, methyl iodide, methyl bromide, methyl chloride, dimethyl carbonate, methyl trifluoromethane sulfonate, and trimethyloxonium tetrafluoroborate.

8. The process of claim 5, wherein the metabisulfite salt is an alkali metal metabisulfite salt.

9. The process of claim 5, wherein the process further comprises preparing the bromo indanone (3) by cyclizing phenylpropionic acid (2)

(2)

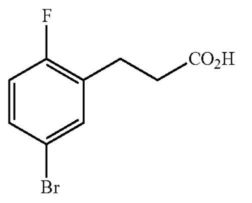

in thionyl chloride in the presence of a Lewis acid to provide the indanone (3).

10. The process of claim 9, wherein phenylpropionic acid (2) is prepared by reacting benzaldehyde (1)

(1)

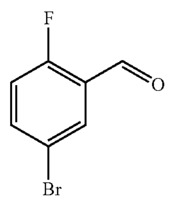

with Meldrum's acid to provide phenylpropionic acid (2).

11. The process of claim 1, wherein step (d) comprises: treating fluorodiol (7) with a deoxyfluorinating agent and a base to provide trifluoro indanol (8)

(8)

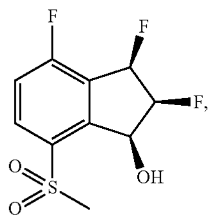

and converting trifluoro indanol (8) to belzutifan.

12. The process of claim 11, wherein step (d) further comprises coupling trifluoro indanol (8) with phenol (9)

(9)

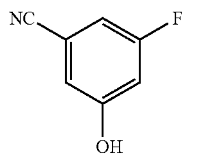

to provide belzutifan.

13. The process of claim 12, wherein the coupling is conducted in an aqueous solution in the presence of a base.

14. The process of claim 12, wherein step (d) further comprises:

treating belzutifan with activated carbon;

recrystallizing decolorized belzutifan from a mixture of a dipolar aprotic solvent and water;

and isolating purified belzutifan.

15. A process for preparing fluorodiol (7)

(7)

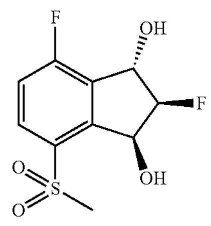

comprising:

(a) contacting hydroxyindanone (5)

(5)

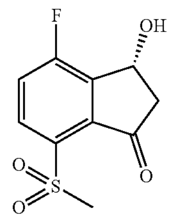

with a fluorinating agent under acidic conditions to yield fluoro hydroxyindanone (6), (6)

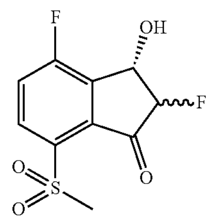

(b) contacting the fluoro hydroxyindanone (6) with a ketoreductase comprising the full-length sequence of SEQ ID NO:2 to provide fluorodiol (7); and (c) isolating the fluorodiol (7).

16. The process of claim 15, wherein step (b) further comprises contacting the fluoro hydroxyindanone (6) with NADP.

17. The process of claim 16, wherein step (b) further comprises contacting the NADP and the fluoro hydroxyindanone (6) with a secondary alcohol.

* * * * *

SEQUENCE LISTING

```
Sequence total quantity: 2
SEQ ID NO: 1            moltype = AA  length = 349
FEATURE                 Location/Qualifiers
source                  1..349
                        mol_type = protein
                        organism = synthetic construct
SEQUENCE: 1
MGSHHHHHHH HGSAALNADT LDMSLFFGTP SQKQDFCDSL LRLLKARGVV KLINHPIPSE  60
SIHELFAQTK RFFNLPLETK MLAKHPEQAL PARGYAFVGQ ENVANISGYE KGLPPLKTRD  120
IKETVDFGSA NDEKYDNLWV PEEELPGFRS FMEGFYELAF KTEMQILEAL AIALGVSPDH  180
LKSLHNRAHS ELRILHYPAI PASELADGTA TRIAEHTDFG SITMLFQDGV GGLQVEDQEN  240
LGTFNNVESA SPTDIILNIG DSLQRLTNDT FKAACHRVTW PPSIKDGDGS EVIPERYSVA  300
YFVKPNRSAS LFPLKEFIEE GVPPKYEDLT FEEWNNRRIE KLFSAEAKA             349

SEQ ID NO: 2            moltype = AA  length = 353
FEATURE                 Location/Qualifiers
source                  1..353
                        mol_type = protein
                        organism = synthetic construct
SEQUENCE: 2
MKKIDNAVLP AGSLVLVTGA NGFVGSHVVE QLLEHGYKVR GTARSASKLA NLQKRWDAKY  60
```

-continued

```
PGRFETAVVE DMLKDGAYDE VIKGAAGVAH IASPVSFSPK YDEVVPPAIG GTLNALRAAA  120
ATPSVKRFVL TSSMMAAIVP KPNVPGIYLD EKSWNLESID KAVTLPESHK EKGLWVYAAS  180
KTMAEMLAWH FMDENKPHFT LNTVLPAYTI GTIFDPETQS GSTSGIVMKL FNGEVSPMLA  240
LFGPQHYVSA FDIGLLHLGC LVLPQIERRR VYGTAAPFDW NMVLAVFRKL WPSKTFPADF  300
PDQGQDLSVF DTRPSLEILK SLGREGWRSF EDSIKDLVGS EFDGQTGHHH HHH         353
```